United States Patent
Madhavamenon et al.

(10) Patent No.: US 10,576,113 B2
(45) Date of Patent: Mar. 3, 2020

(54) METHOD OF PREPARING STABLE, WATER SOLUBLE PROBIOTIC COMPOSITIONS BASED ON MILLETS AND SIMILAR CEREALS

(71) Applicant: Akay Flavours and Aromatics Pvt, Ltd, Cochin (IN)

(72) Inventors: Krishnakumar Illathu Madhavamenon, Cochin (IN); Balu Paulose Maliakel, Cochin (IN)

(73) Assignee: AKAY FLAVOURS & AROMATICS PVT, LTD., Kerala (IN)

( * ) Notice: Subject to any disclaimer, the term of this patent is extended or adjusted under 35 U.S.C. 154(b) by 0 days.

(21) Appl. No.: 15/490,450

(22) Filed: Apr. 18, 2017

(65) Prior Publication Data
US 2017/0296598 A1 Oct. 19, 2017

(30) Foreign Application Priority Data
Apr. 19, 2016 (IN) ............... 201641013544

(51) Int. Cl.
| | |
|---|---|
| A61K 35/747 | (2015.01) |
| A61K 9/16 | (2006.01) |
| A61K 36/064 | (2006.01) |
| A61K 9/00 | (2006.01) |
| A23L 2/02 | (2006.01) |
| A23L 33/135 | (2016.01) |
| A23L 2/66 | (2006.01) |
| A23P 10/30 | (2016.01) |
| A23L 2/52 | (2006.01) |
| A61K 36/899 | (2006.01) |
| A23C 9/13 | (2006.01) |
| A61K 35/00 | (2006.01) |
| A61K 9/19 | (2006.01) |

(52) U.S. Cl.
CPC .......... *A61K 35/747* (2013.01); *A23C 9/1315* (2013.01); *A23L 2/02* (2013.01); *A23L 2/52* (2013.01); *A23L 2/66* (2013.01); *A23L 33/135* (2016.08); *A23P 10/30* (2016.08); *A61K 9/0095* (2013.01); *A61K 9/1664* (2013.01); *A61K 36/064* (2013.01); *A61K 36/899* (2013.01); *A61K 9/19* (2013.01); *A61K 2035/115* (2013.01)

(58) Field of Classification Search
CPC .. A61K 35/747; A61K 9/0095; A61K 9/1664; A61K 36/064; A61K 36/899; A61K 9/19; A61K 2035/115; A23P 10/30; A23L 33/135; A23L 2/02; A23L 2/52; A23L 2/66; A23C 9/1315
USPC ........................................ 435/243
See application file for complete search history.

(56) References Cited

U.S. PATENT DOCUMENTS

| | | | |
|---|---|---|---|
| 6,468,525 B1 | 10/2002 | Watson et al. | |
| 2006/0172040 A1* | 8/2006 | Tilley | A21D 8/042 426/94 |
| 2008/0193485 A1 | 8/2008 | Gorbach et al. | |
| 2012/0107395 A1* | 5/2012 | Xie | A61K 35/741 424/452 |
| 2012/0263826 A1 | 10/2012 | Fang et al. | |
| 2013/0136826 A1 | 5/2013 | Penhasi | |

OTHER PUBLICATIONS

Livestrong.com, Recommended Dosage for Probiotics, Accessed Jan. 15, 2019, Online at: www.livestrong.com/article/367869-recommended-dosage-for-probiotics/.*
David, Bwai Macham et al. "Proximate composition, mineral and phytochemical constituents of *Eleusine coracana* (finger millet)." *International Journal of Advanced Chemistry*, 2 (2) (2014) 171-174.
Govender, Mershen et al. "A Review of the Advancements in Probiotic Delivery: Conventional vs. Non-conventional Formulations for Intestinal Flora Supplementation." *AAPS PharmSciTech*, vol. 15, No. 1, Feb. 2014.
Mortazavian, Amir Mohammad et al. "Delivery of Probiotic Microorganisms into Gastrointestinal Tract by Food Products." *New Advances in the Basic and Clinical Gastroenterology*, Ch. 6, 121-146.

* cited by examiner

*Primary Examiner* — Jennifer M. H. Tichy
(74) *Attorney, Agent, or Firm* — Brinks Gilson & Lione

(57) ABSTRACT

The probiotic powder compositions comprising probiotic microorganisms encapsulated in nutritional rich cereal powder matrix. Encapsulation of probiotics in cereal powders offers nutritive and health benefits to the consumer. The present invention further includes methods of making and using the probiotic powder compositions of the invention. The powder compositions are stable, maintains the viability of probiotic microorganisms in various formulations.

15 Claims, 11 Drawing Sheets

METHOD OF PREPARING STABLE, WATER SOLUBLE PROBIOTIC COMPOSITIONS BASED ON MILLETS AND SIMILAR CEREALS

CROSS-REFERENCE TO RELATED APPLICATION

The present application claims priority to Indian Provisional Patent Application No. IN201641013544 filed on Apr. 19, 2016, the full disclosure of which is hereby incorporated by reference herein.

FIELD OF THE INVENTION

The present invention relates to the field of probiotic compositions and more particularly the present invention relates to a method for preparing probiotic compositions comprising preparation of nutritionally rich cereal extracts from cereal grains, growing and encapsulation of probiotic strains into said cereal extract to provide a stable food grade and water soluble probiotics powder, suitable for ambient storage conditions.

BACKGROUND OF THE INVENTION

Keeping good digestive health is essential to our overall wellbeing and feeling healthy. Recently there has been developed a great concern among people about proper diet and health. Foods we eat have a vital role in ameliorating and creating bowel diseases. Health care experts consider many of the health problems are related to gut, majorly due to the issues associated with improper digestion. Our gastrointestinal tract contains more than 400 different beneficial bacteria species, commonly referred as the intestinal microflora, which support in assimilation, synthesis of vitamin, nutrients and also helpful for proper functioning of the gut. It has an important role in the host immune system and helps the host by maintaining the physiological, nutritional and immunological system. Human gastrointestinal system is a balance of beneficial and harmful bacteria and it is necessary to maintain a bacterial balance. Modern lifestyle and increased use of drugs will have an adverse effect on the natural flora of gut. This could be overcome by the consumption of beneficial live bacteria known as probiotics.

Probiotics are live microorganisms which when administrated in adequate amounts confer a health benefit on the host. Many commercial products based on probiotics are available in the market in a variety of matrices like frozen desserts, yoghurt and beverages. Yoghurt is the most common probiotic carrying food, and it is extended to other products like fermented milk, juices, nutrition bars, etc. It has also been marketed in the form of dietary supplements, medical foods and drugs. In ancient Indian society, it was commonplace to enjoy a form of yoghurt drink called 'Lassi' before dinner. These Indian traditions were based on the principle of using sour milk as a probiotic delivery system.

Finger millet is an important variety of millets grown widely in India and Africa. It is considered as a Nutri-cereal because of its good nutritional values, easy availability, low cost. Finger millet carbohydrates contain 1-2% free sugars, 75-80% starch and non-starchy polysaccharides. It has a good shelf life due to its high polyphenol content (David et al., 2014, 2, 171). It is easy to digest and does not contain gluten; people who are sensitive to gluten can easily consume finger millet.

Many of the products available in the market containing probiotic bacteria as free probiotic cells have poor viability. Viability of probiotic bacteria is affected by many parameters including low pH, hydrogen peroxide, dissolved oxygen content, storage temperature, strains etc. (Mortazavian et al., 2012, *In tech. In book—new advances in the basic and clinical gastroenterology*). Several attempts were made in the past to increase the viability of probiotic bacteria, which include selection of acid and bile resistant strains, two step fermentation, stress adaptation, incorporation of micronutrients and microencapsulation (Govender et al., 2014). Though techniques such as liposome coating, coacervation, co-crystallization, molecular inclusion have been well studied, the high cost and the lack of credibility as 100% natural and food-grade formulation, especially from food components such as cereals are limitations. Another probiotic encapsulation technique using calcium alginate was also common in the prior art due to its merits such as non-toxicity, biocompatibility and low cost. But this technology had some limitations due to high sensitivity of alginate beads especially in the acidic conditions.

US 2013/0136826 A1 discloses a healthy liquid probiotic with a heat treatment in one stage of its preparation. Though there are techniques to maintain sufficient amount of probiotic microorganisms with the ability to resist heat and humidity, it was achieved by the use of chemicals and other additives. This technology was also not focusing on enhancing the shelf life stability of probiotic strains.

U.S. Pat. No. 6,468,525 B1 discloses a novel probiotic food supplement contains a mixture of five beneficial microflora with added macromolecules. But there is no evidence for the microbiota and the technology was not focusing on enhancing the stability of the composition.

US 2012/0263826 A1 discloses a procedure for encapsulation of probiotics. This technology limits its scope due to the use of synthetic polymers for the encapsulation.

US 2008/0193485 A1 discloses a food product containing probiotic and β glucan isolated from a natural source. However this record is not focusing on any enhancement of storage stability.

Hence there exists a need for safe, healthy and functional food components, especially from those derived from cereals, fruits, vegetables etc., which can be used both as a medium for the growth of probiotics to the desired concentrations and as a material for the stable formulation as micro encapsulates or the like. A suitable process, especially the one without using any organic solvents or synthetic excipients for the preparation of such materials for probiotics growth and encapsulation is also of great significance. Availability of such material, its universal acceptance as a food item, its taste and other organoleptic properties for food/beverage purpose and finally the cost play important role in such inventions. Thus in the present invention, widely known, highly nutritious, diabetic friendly, inexpensive cereals like finger millet is selected as the raw material of choice, from which a unique composition of water extract that can be further used for both growth and stable encapsulation of probiotic strains as water soluble powder suitable for food, dietary supplements, nutritional supplements, pharmaceutical applications etc. There is also a need exists to develop a stable probiotic formulation suitable for ambient conditions of storage and useful as a food supplement, dietary supplements or nutritional supplements to provide beneficial probiotic bacteria and to assist proper functioning of intestinal tract

SUMMARY OF THE INVENTION

The present invention relates to compositions and method of preparing food grade probiotic compositions comprising healthy cereal extracts and probiotic strains, wherein said method comprising incorporation of probiotic strains into aqueous extracts of the cereals, wherein at least one of said cereals is selected from finger millet (Ragi), amaranth, rye, wheat, barley, rice, or any other suitable cereals thereof.

In an embodiment, the present invention provides a method for preparing dried probiotic powder composition comprising
a) extracting flaked and/or powdered cereal powder with water to prepare the filtrate;
b) wherein extracting flaked cereal powder with water is repeated for 4-7 times for 30 minutes at ambient temperature;
c) inoculating probiotic microorganism strains to the filtrate obtained in step (b);
d) incubating the mixture obtained in step (c) at 37±5° C. to provide desired microbial growth;
e) subjecting the probiotic cereal mixture obtained in step (d) to spray drying/freeze drying to provide encapsulated probiotic powder.
The process is depicted in the flow chart shown in FIG. 13.

DETAILED DESCRIPTION OF THE INVENTION

Figure 1:
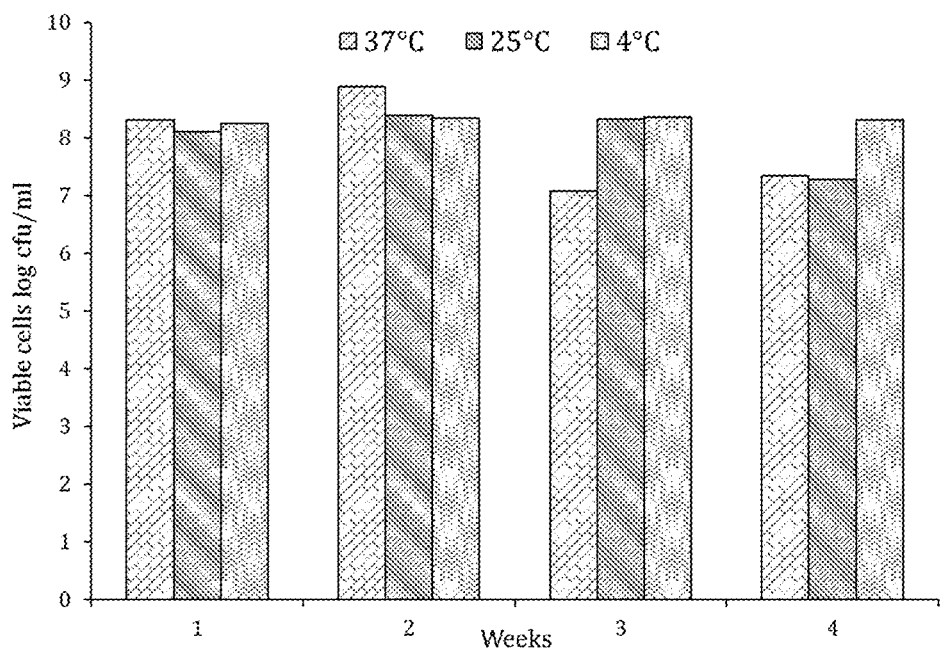
FIG. 1—shows temperature stability of *Lactobacillus acidophilus* at 4, 25 and 37° C.
Figure 2:
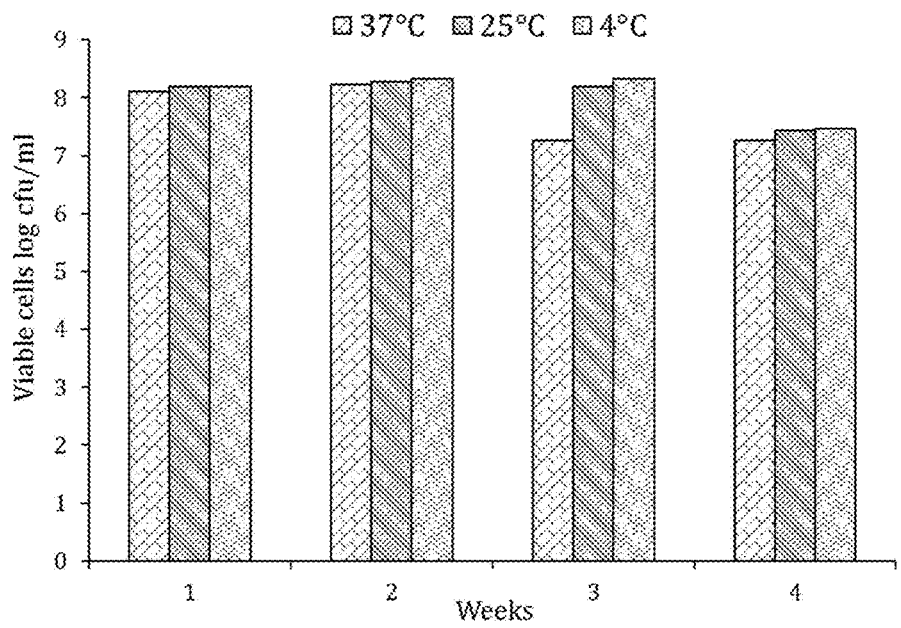
FIG. 2—shows temperature stability of *Lactobacillus brevis* at 4, 25 and 37° C.
Figure 3:
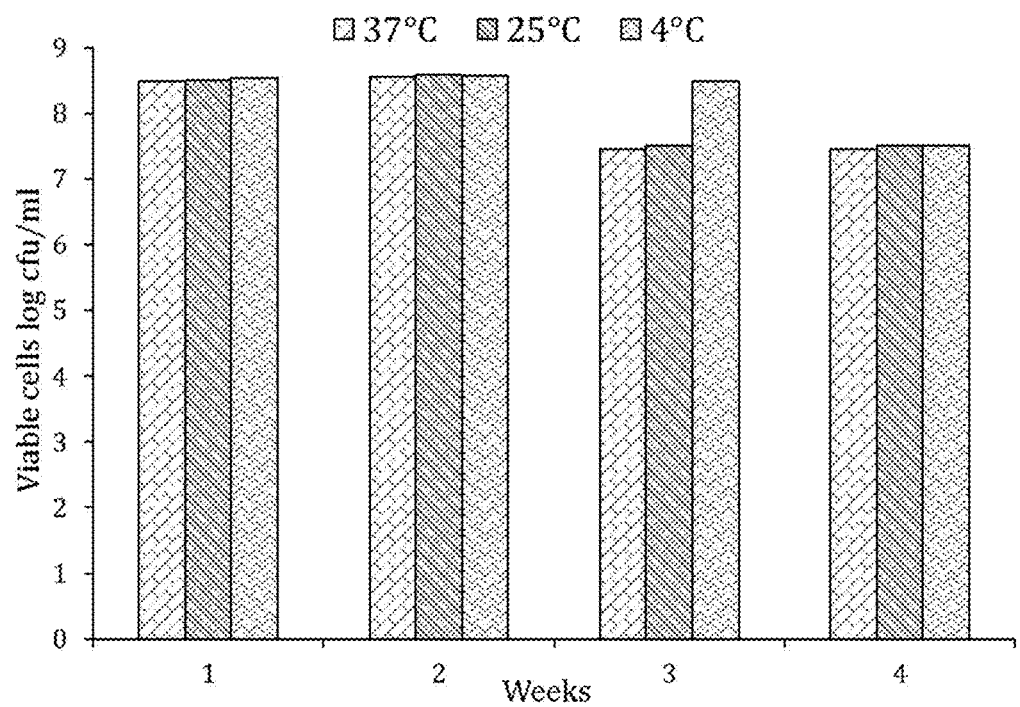
FIG. 3—shows temperature stability of *Saccharomyces cerevisiae* at 4, 25 and 37° C.

The terms "Ragi", "Finger millet", "*Elusine coracana*", constitutes same meaning, are being used interchangeably throughout the document.

The terms "Barley", "*Hordeum vulgare*", constitutes same meaning, are being used interchangeably throughout the document.

The terms "Wheat", "*Triticum*", constitutes same meaning, are being used interchangeably throughout the document.

The terms "Amaranth", "*Amaranthus caudatus*", "*Amaranthus cruentus*", "*Amaranthus hypochondriacus*", constitutes same meaning, are being used interchangeably throughout the document.

In an embodiment, the present invention relates to the probiotic microorganism powders.

In an embodiment, the dried powder composition comprising the probiotic microorganisms and carrier phase.

In an embodiment, the probiotic microorganisms include bacteria and yeast. In a further embodiment the probiotic bacteria is selected from the group consisting of *Lactobacillus acidophilus, Lactobacillus brevis, Lactobacillus rhamnosus GG, Lactobacillus bulgaricus, Lactobacillus plantarum, Lactobacillus reuteri, Lactobacillus casei, Lactobacillus paracasei, Bifidobacterium infantis, Bifidobacterium lactis, Bifidobacterium bifidum, Streptococcus thermophiles, Bacillus coagulans* or a combination thereof.

In yet another embodiment, the probiotic yeast is selected from the group consisting of *Saccharomyces cerevisiae, Saccharomyces boulardii* or a combination thereof.

The probiotic microorganisms when consumed provides various health benefits. Each of the probiotic microorganisms will be responsible for the specific activity. The above list does the limit the scope of invention, microorganisms are selected based on their activity to provide the desired effect.

In an embodiment, the carrier phase contains cereal powder wherein the cereal powder comprises at least one substance selected from the group consisting of ragi, wheat, barley, amaranth, rye, rice or a combination thereof.

In an embodiment, the present invention comprising a method for the preparation of probiotic composition from cereal extracts and probiotic strains, wherein said method comprising encapsulation of probiotic strains into the cereal grain extracts.

In an embodiment, cereal extract prepared acts as the growth medium for probiotic microorganisms. The cereal grains of choice are flacked using a flaker to obtain a cereal flakes. The cereal flakes are dispersed in water at a ratio of 1:3, followed by extraction in a stainless steel vessel with an agitator. Water is added to said powder to prepare a uniform slurry. The slurry is then heated and subjected to continuous washing process, wherein each wash is filtered and collected in a separate tank. The extraction process is repeated 4-7 times for 30 min at an ambient condition. The obtained solution is filtered and kept for further use.

The method primarily involves extraction of a unique composition of carbohydrates and proteins from cereal grains using water extraction technique.

In an embodiment, the extraction can also be carried out under the application of ultrasound and/or microwave to the water slurry of millets. Alternatively, water extraction can also be performed in a continuous extractor for high throughput and commercial viability.

In an embodiment, the filtered water extract thus obtained can be concentrated and converted in to powder form by employing at least one of the drying techniques selected from spray drying, freeze drying, drum drying, radiation drying or any other technique suitable for the evaporation of water thereof. The free flowing powder prepared from this process is suitable for long term storage and used as matrix in which the probiotic strains can be grown to high levels. When the required growth is obtained, the same extract can be used to encapsulate the bacteria to form stable free flowing powder.

In an embodiment, the filtrate obtained in the above process is inoculated with probiotic microbial strains of choice and incubated at 37±5° C. for the duration effective to achieve required amount of growth, preferably 20 to 72 hours and most preferably 24 to 48 hours.

The process of inoculation of microorganism and incubation not only allow the microorganism to grow, also encapsulates the probiotic microorganism. The filtrate after achieving effective amount of probiotic microbial growth, is subjected to spray drying or freeze drying or any other technique suitable for microorganisms to obtain free flowing powder.

In an embodiment, the present invention provides a method for growing probiotic strains in cereal extract without using any additives. The unique advantage of cereal extract as it acts as growth medium and encapsulating agent for probiotic microorganisms.

In an embodiment, the liquid extract directly obtained from water extraction process of cereals or its free flowing extract powder dissolved in water can be used for inoculation and bacterial growth.

In an embodiment, the homogenization of the microorganism grown water extract of cereals can be subjected to homogenization under pressure or under rotor-stator equipment for effective encapsulation of the microorganisms in cereal matrix.

The present invention further provides a method for preparing a stable free flowing powder from cereal extract and probiotic strain growth mixture without using any additives. Said method involves drying of said cereal extract and probiotic strain growth mixture using a method selected from spray drying, freeze drying, or any other suitable drying techniques or combinations thereof.

In an embodiment, the inlet temperature during spray drying is about 100° C. to 120° C., preferably 110° C.

In an embodiment, the outlet temperature is preferably below the inlet temperature, the outlet temperature is about 75° C. to 95° C., preferably about 85° C. The outlet temperature and the solution was constantly stirred throughout the process with a magnetic stirrer.

In some embodiments, the inlet or outlet temperatures may be varied, if necessary, depending on the water evaporation capacity, design, gas, or other experimental parameters.

In an embodiment, the dried powder composition comprises at least one bacteria and one yeast strains.

In yet another embodiment, the dried powder composition comprises at least two bacteria and yeast strains.

In a preferred embodiment, the dried powder composition comprises *L. acidophilus, L. brevis* and *S. cerevisiae*.

The powdered probiotic composition of the present invention is stable under ambient storage conditions as well as gastrointestinal conditions.

In an embodiment, the encapsulated probiotic powder composition obtained by the above process is found stable and suitable to use in juices, yoghurts, milk, tablets, caplets, capsules, functional food supplement, dietary supplement, food/beverage ingredient or other pharmaceutical formulations.

In an embodiment, the probiotic powder composition exhibits good water solubility and provides a concentration of probiotic stains ranging from $1\times10^3$ to $1\times10^{12}$ cfu/g.

The viability of the probiotic organisms in the powder compositions is determined by diluting 1 gm of powder with 9 ml sterile saline solution. From this solution several dilutions were made and 1 ml of each one was dispersed in Petri plates containing MRS (*Lactobacillus* species) and MGYP (*S. cerevisiae*) agar. The plates were incubated at 38° C. for 48 hr. After completion of the specified period of incubation, the colonies were counted and the results are reported.

The initial counts of all microencapsulated powders were between 8 to 8.5 log 10 CFU/g after spray drying (Table 1). The results showed that Ragi is a good medium for the growth of probiotics.

TABLE 1

Viability of microencapsulated probiotics before and after incorporation to ragi extract.

| Encapsulated matrix | Initial count | Before spray drying (with ragi) | After spray drying |
|---|---|---|---|
| L. acidophilus | 8.04 | 8.34 | 8.30 |
| L. brevis | 8.07 | 8.11 | 8.09 |
| S. cerevisiae | 8.04 | 8.54 | 8.49 |

Note:
All values in log10 CFU/g

In an embodiment the probiotic powder compositions obtained by the above process are subjected to stability test. The encapsulated probiotic powders are stored at controlled temperatures of 4° C., 25° C. and 37° C. Samples are evaluated weekly for a period of 30 days to evaluate the stability of the dried powder compositions.

The samples obtained at various intervals has been evaluated for cell counts, identified that 25° C. and 4° C. are the best temperature for the storage of probiotics. The cell count shows fluctuation while stored at room temperature. The probiotic organisms have good survival when stored at low temperatures. The viability of probiotic organisms is not significantly affected by temperature, indicating the stability of formulation. The results as shown in FIG. 1, 2, 3.

Figure 4:
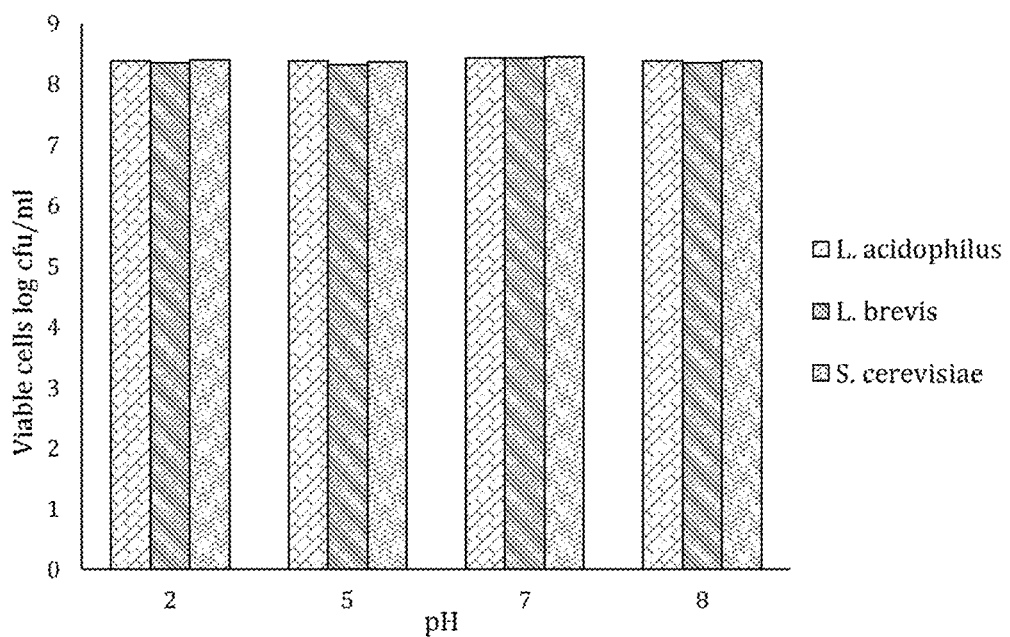
FIG. 4—shows probiotic microorganism count at different pH.

In an embodiment, the viability of probiotic powder compositions are evaluated at varied pH. The *Lactobacillus acidophilus* released from the ragi extract is treated to acid challenge conditions at pH 2.0, 5.0, 7.0 & 8.0 at room temperature. Ragi extract (9 ml) is adjusted to the above pH by using 2.0M HCl and 0.5M NaOH. To the pH adjusted extract, 10 ml of probiotic suspension is added through stirring. After 24 h and 48 h of addition, number of viable surviving bacteria is determined by plate counting after anaerobic incubation at 37° C. for each time tested. Replicate plates were counted at each time interval during the survival study, and then repeated in duplicate. The results as shown in FIG. 4

In an embodiment, the degree of crystallinity, stability and nature of entrapment of probiotics in the ragi matrix are analysed by performing powder X-ray diffraction studies (PXRD) on a Bruker D8 Advance instrument (Bruker AXS GmbH, Karlsruhe, Germany); solid state Fourier transform spectroscopy (FTIR) on Avatar 370 model instrument (Thermo Nicolet Corporation, Madison, USA); and scanning electron microscopy (SEM) using a Jeol 6390 LA equipment (JEOL Ltd, Tokyo, Japan).

Figure 5A:
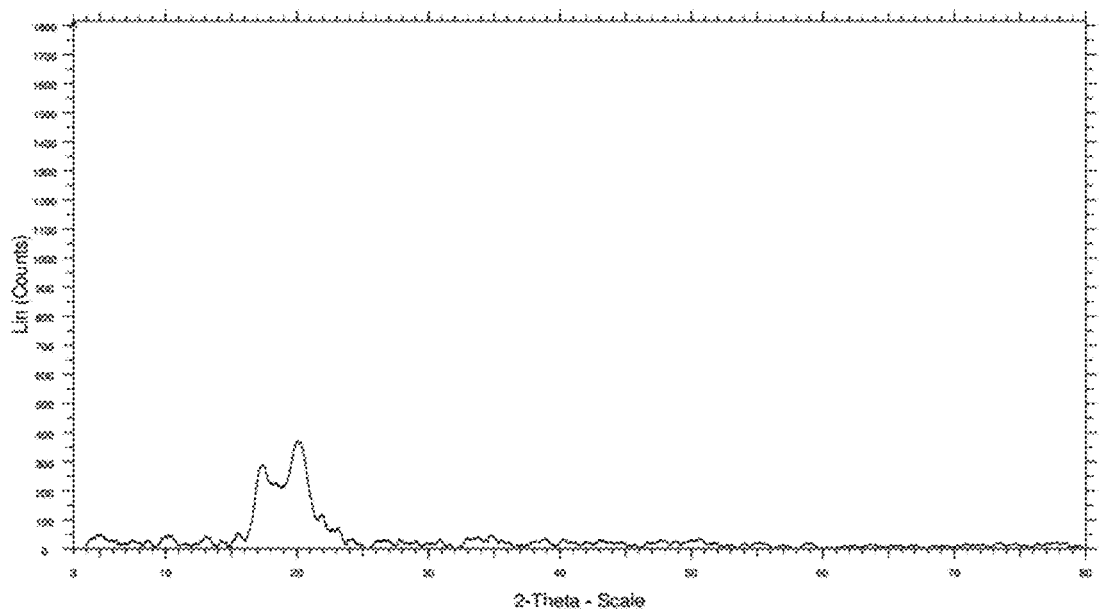
FIG. 5A—shows PXRD of encapsulated probiotics in the ragi matrix
Figure 5B:
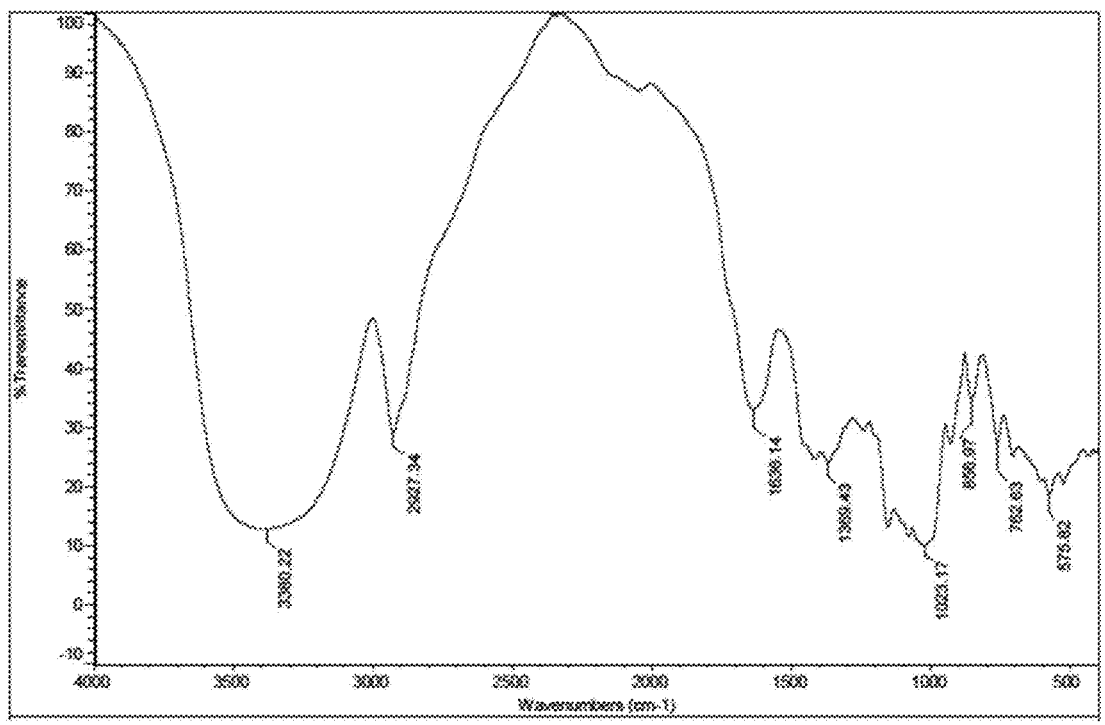
FIG. 5B—shows FTIR spectrum of encapsulated probiotics in the ragi matrix
Figure 6A:
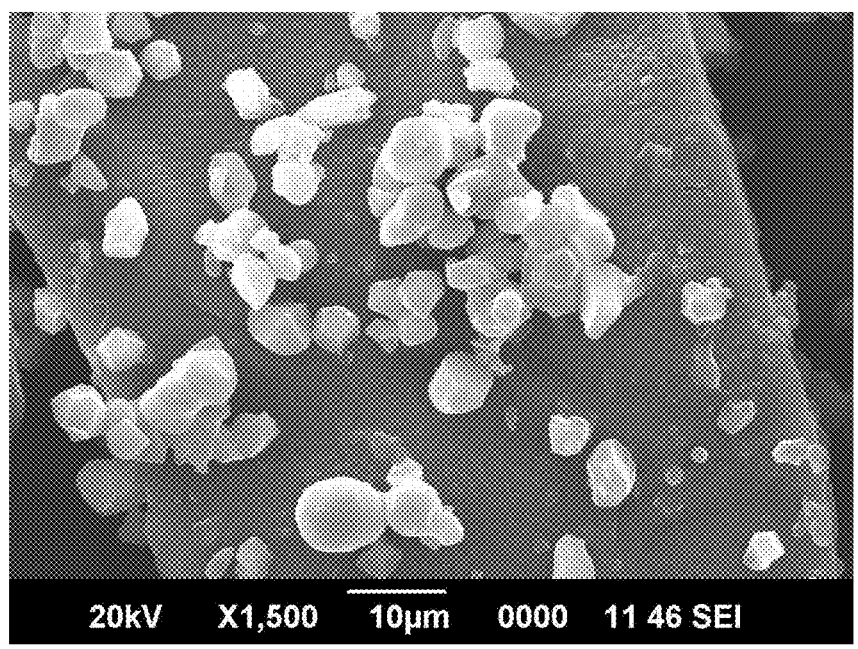
FIG. 6A—shows SEM of encapsulated *Lactobacillus acidophilus* in the ragi matrix FIG. 6B—shows SEM of encapsulated *Saccharomyces cerevisiae* in the ragi matrix FIG. 7A—shows viable cell counts in Guava fruit beverages at 4° C.
Figure 6B:
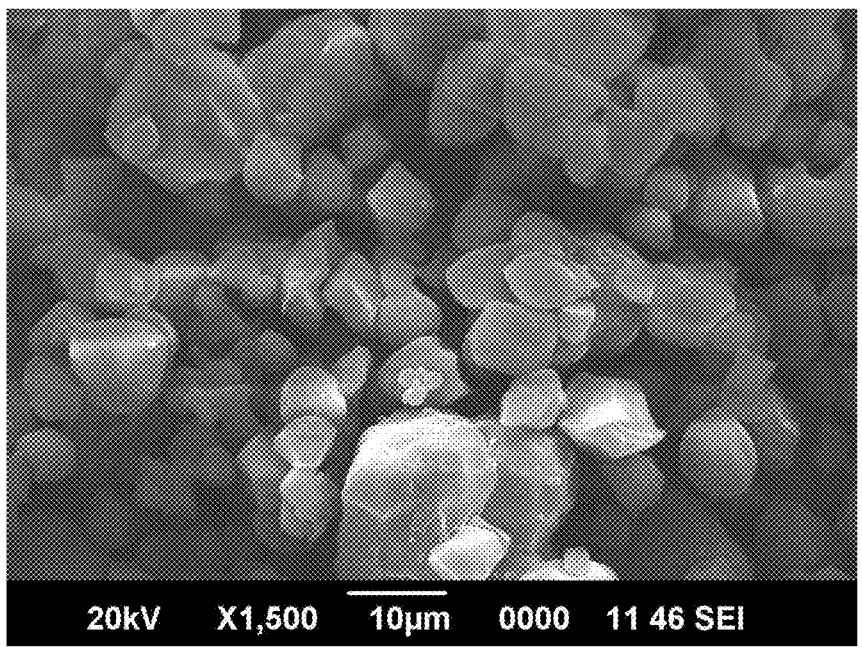
Figure 7A:
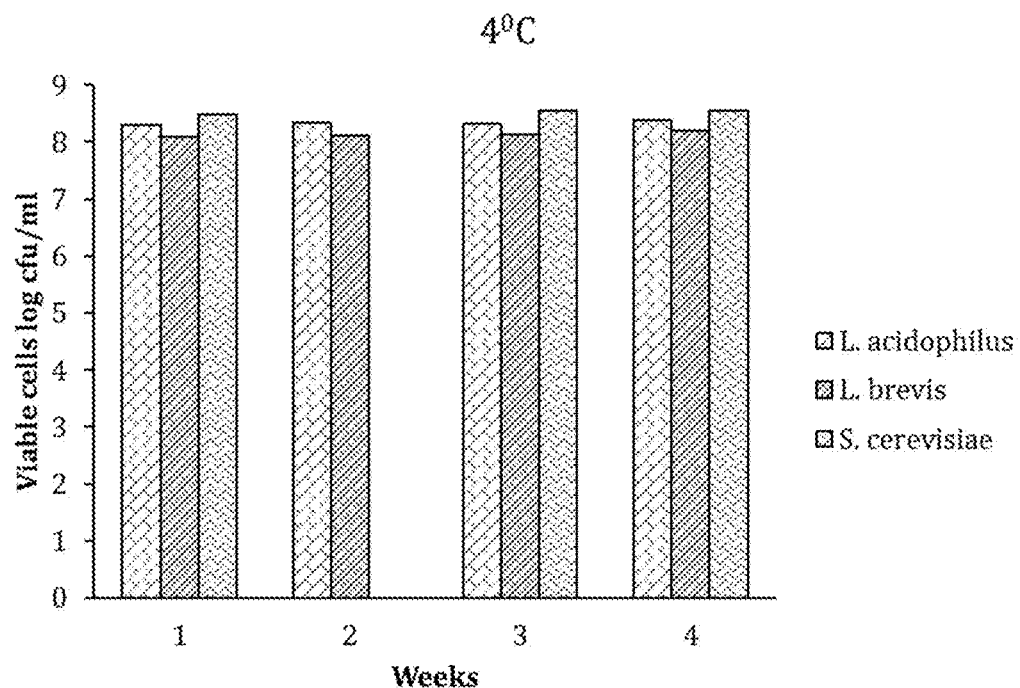
FIG. 7B—shows viable cell counts in Guava fruit beverages at 30° C.
Figure 7B:
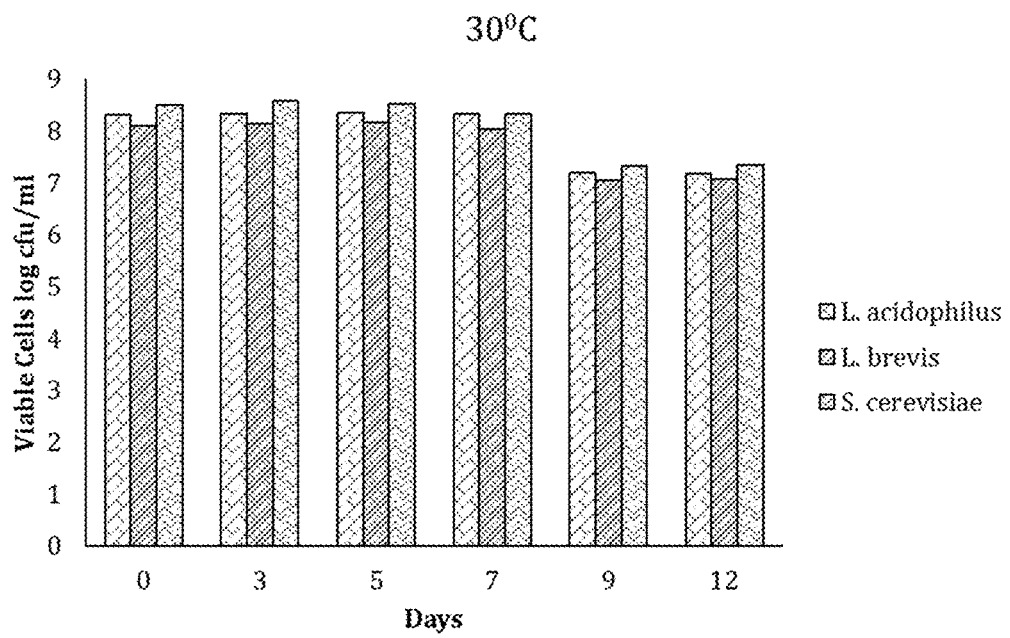
Figure 8A:
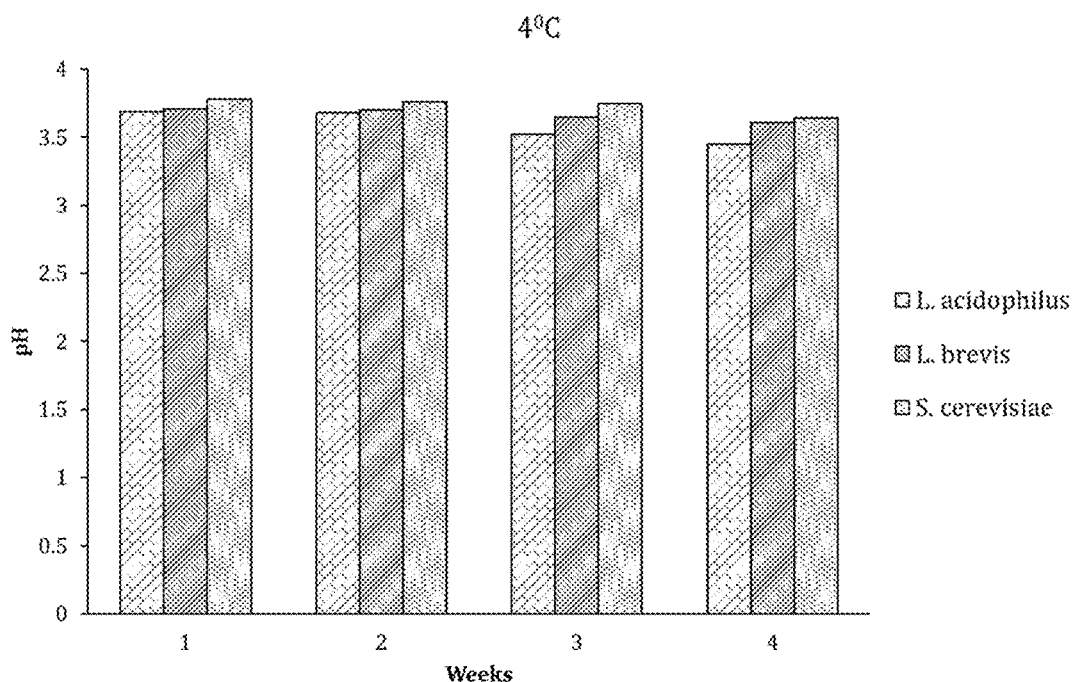
FIG. 8A—shows pH variability in Guava fruit beverages at 4° C.
Figure 8B:
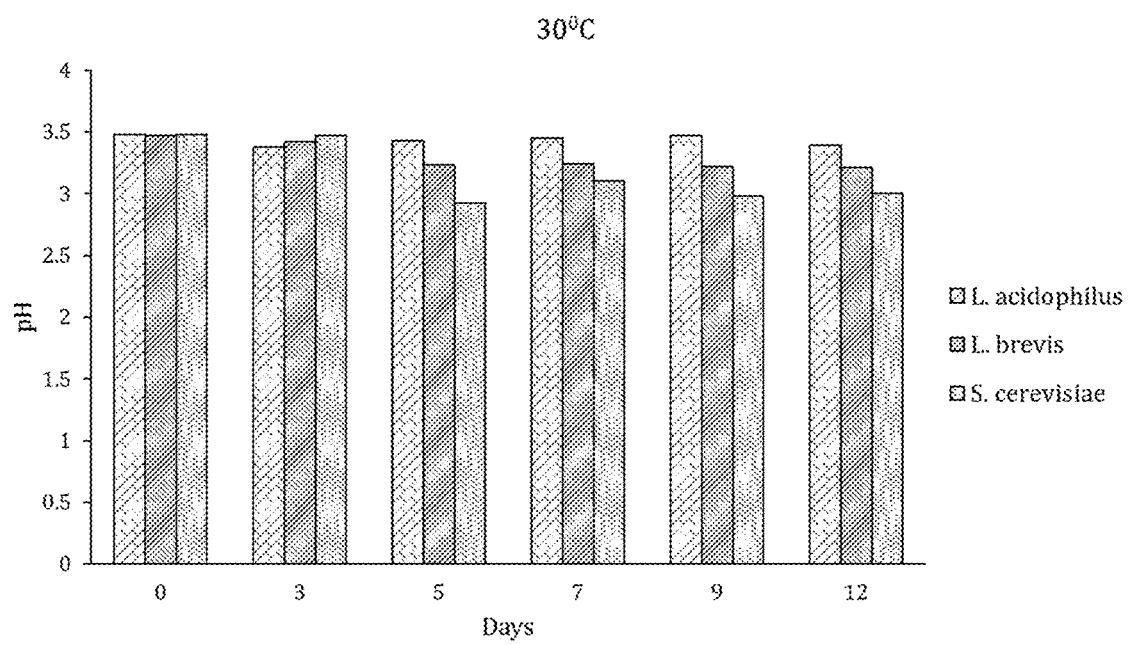
FIG. 8B—shows pH variability in Guava fruit beverages at 30° C.
Figure 9A:
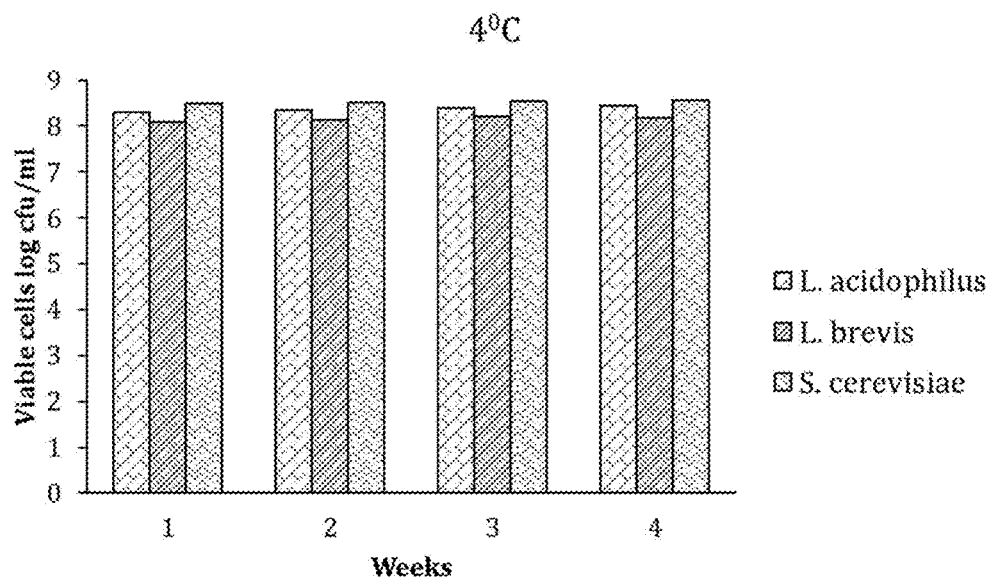
FIG. 9A—shows viable cell counts in Apple fruit beverages at 4° C.
Figure 9B:
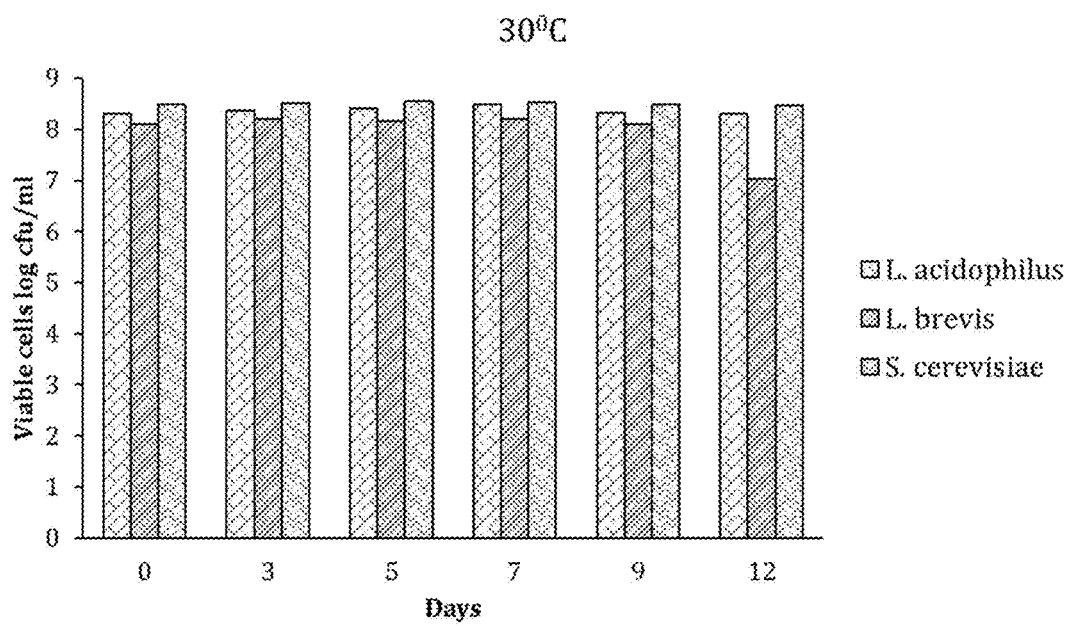
FIG. 9B—shows viable cell counts in Apple fruit beverages at 30° C.
Figure 10A:
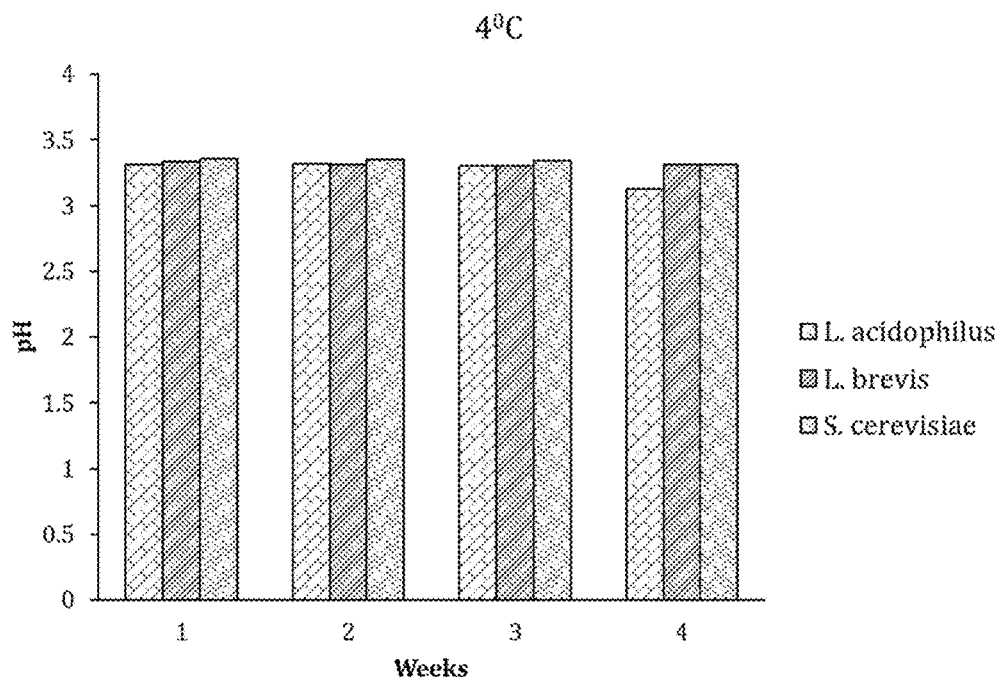
FIG. 10A—shows pH variability in Apple fruit beverages at 4° C.
Figure 10B:
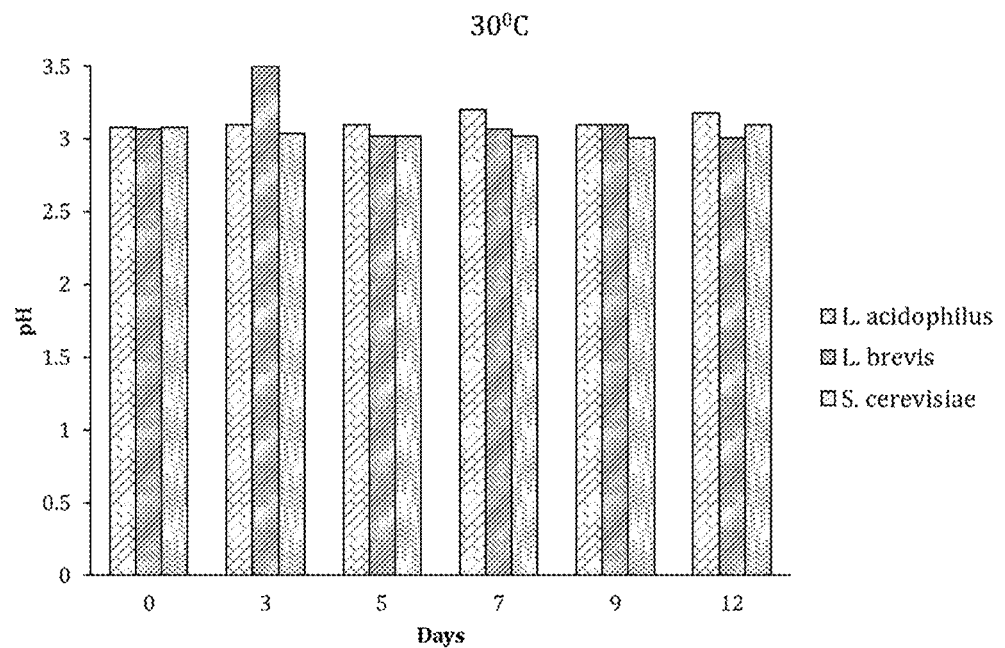
FIG. 10B—shows pH variability in Apple fruit beverages at 30° C.
Figure 11A:
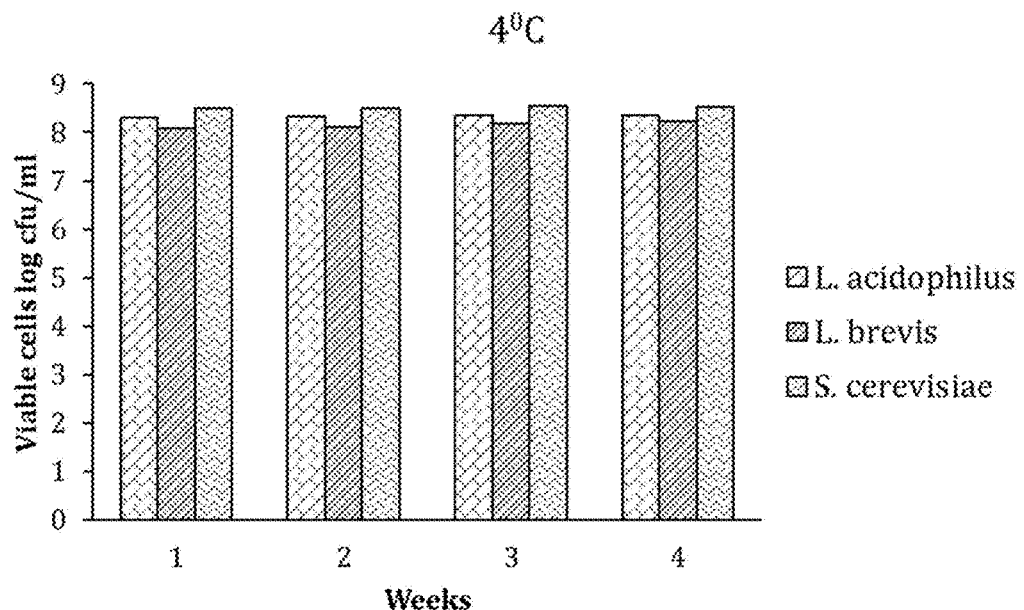
FIG. 11A—shows viable cell counts in Mango fruit beverages at 4° C.
Figure 11B:
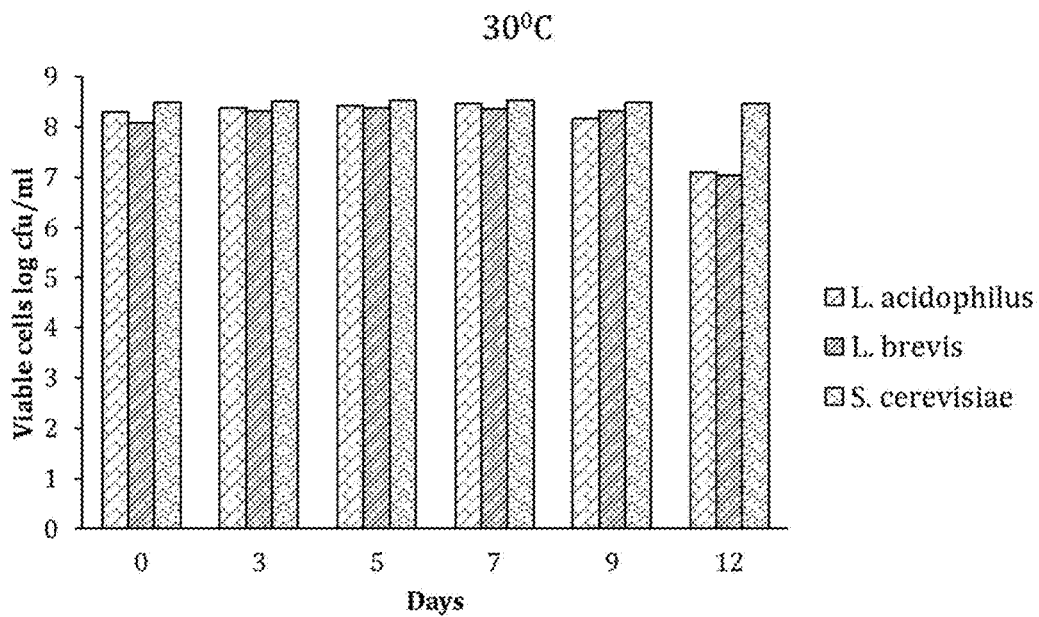
FIG. 11B—shows viable cell counts in Mango fruit beverages at 30° C.
Figure 12A:
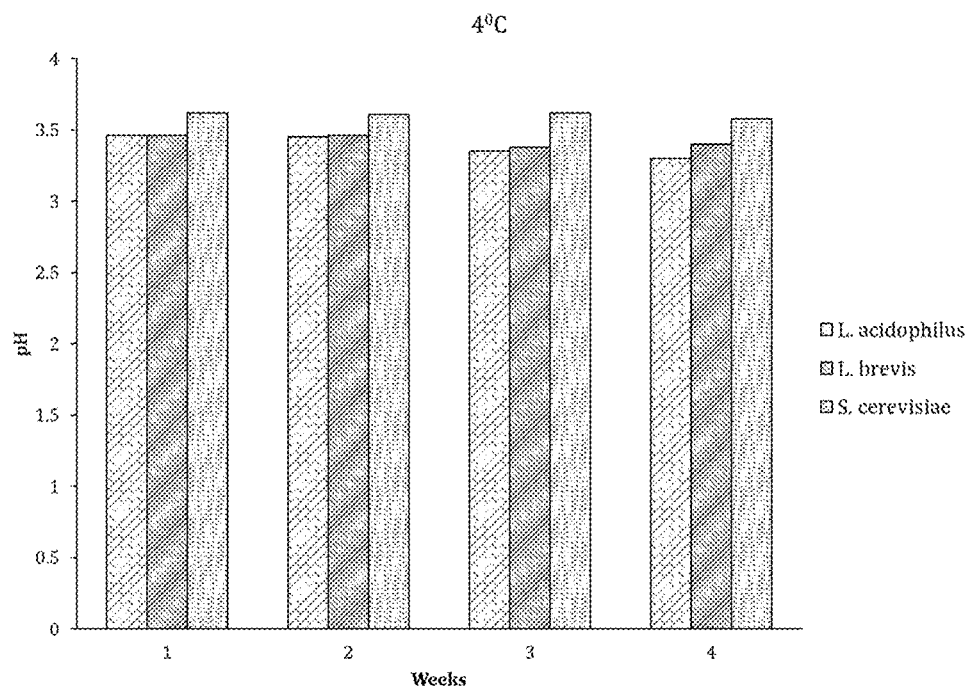
FIG. 12A—shows pH variability in Mango fruit beverages at 4° C.
Figure 12B:
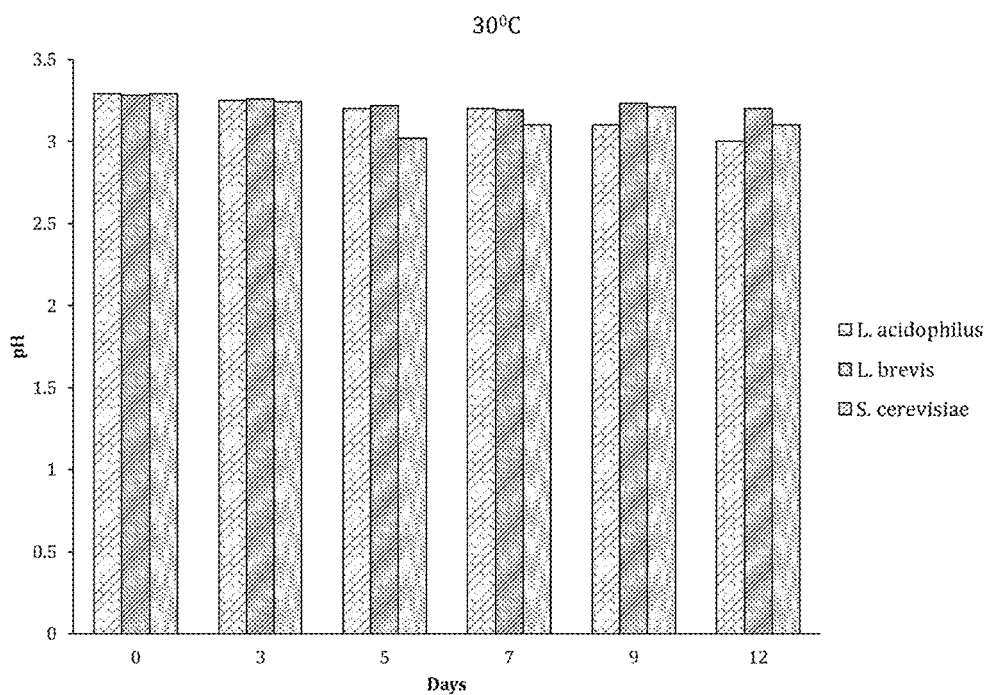
FIG. 12B—shows pH variability in Mango fruit beverages at 30° C.
Figure 13:
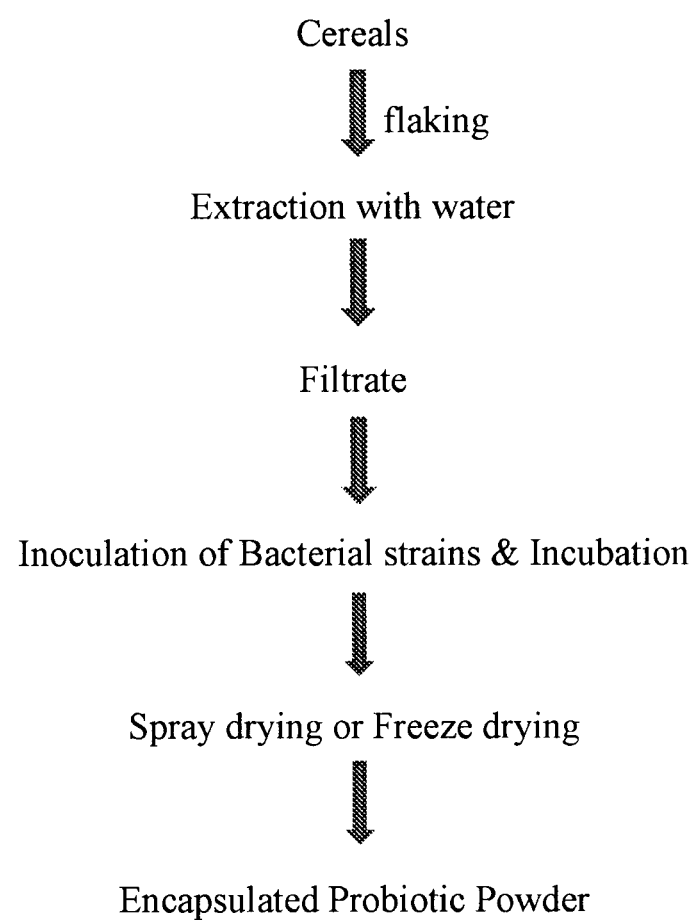
FIG. 13—shows the flow chart for the process described in paragraph [0013] above.

In an embodiment, crystallinity is assessed by Powder X-ray diffraction (PXRD) studies. It showed typical amorphous pattern with just a broad less intense hill around 20° 2θ scattered angle, with very low intensity (FIG. 5A). FTIR peaks of the probiotics encapsulated in ragi extract matrix (FIG. 5B) is similar to the ragi matrix before encapsulation, a characteristic pattern of the water extracted carbohydrate rich fraction from cereals. The amorphous nature of the probiotics encapsulated in ragi extract matrix is further clear from the smooth spherical particles of 2±0.5 µm as evident from SEM studies (FIG. 6A, B).

In addition to dairy products some nondairy products like fruits, vegetables are also used for the probiotic applications. Fruits and vegetables can be considered good matrices, as they contain nutrients like minerals, vitamins, dietary fibers and antioxidants etc. While selecting the appropriate fruits, vegetables various factors like fruit type, the fruit content, the pH, the sugar content and the other components present are considered. Also, processing parameters play a vital role for the survival of probiotics. In the present study, probiotics (microorganisms) encapsulated in Ragi matrix in powder form is added to various juices (Mango, Guava, Apple). On storage, it has been found that the probiotic strains have significant stability in these juices.

Hereinafter, embodiments of the present invention will be described in more detail with reference to the following examples. However, it should be understood that the following examples are provided only for illustrating the present invention and should not be construed as limiting the scope and spirit of the present invention.

Example 1

Preparation of Ragi-Probiotic Powder Composition by Spray Drying.

The ragi (*Elusine coracana*) grains of about 500 gm are flaked using a flaker and the flaked ragi powder is dispersed in Milli Q water in the ratio of 1:3. The mixture is extracted in a stainless steel vessel with an agitator. The extraction process is repeated for 4-7 times for 30 minutes at and ambient temperature condition to yield the desired nutrient profile in the extract.

The ragi extract is rich in the nutrients, which also acts as a growth medium for the probiotic microorganism. The ragi extract contains Carbohydrates 65-75%, Protein 5-8%, Fat 1-2%, Dietary fibre 15-20%, Minerals 2.5-3.5%.

The ragi extract is inoculated with 3 different strains namely *Lactobacillus acidophilus, L. brevis* and *S. cerevisiae* and incubated at 37±5° C. to provide desired microbial growth.

Ragi extract containing *L. acidophilus, L. brevis* and *S. cerevisiae* were spray dried to yield a pale white free flowing powder at a temperature of 110±1° C., at a feed flow rate of 4.1 ml/min. The outlet temperature is 85° C. and the solution is constantly stirred throughout the process with a magnetic stirrer. The resulted free flowing probiotic powder is stored in air tight container.

Example 2

Preparation of Ragi-Probiotic Powder Composition by Freeze Drying.

The ragi (*Elusine coracana*) grains of about 500 gm are flaked using a flaker and the flaked ragi powder is dispersed in Milli Q water in the ratio of 1:3. The mixture is extracted in a stainless steel vessel with an agitator. The extraction process is repeated for 4-7 times for 30 minutes at and ambient temperature condition to yield the desired nutrient profile in the extract.

The ragi extract is rich in the nutrients, which acts as a growth medium for the probiotic microorganism. The ragi extract contains Carbohydrates 65-75%, Protein 5-8%, Fat 1-2%, Dietary fibre 15-20%, Minerals 2.5-3.5%.

The ragi extract is inoculated with 3 different strains namely *Lactobacillus acidophilus, L. brevis* and *S. cerevisiae* and incubated at 37±5° C. to provide desired microbial growth. It was then homogenized for 5 min using a rotor-stator type homogenizer at 20,000 rpm for 5 min.

Ragi extract containing *L. acidophilus, L. brevis* and *S. cerevisiae* were then frozen to −40 to −50° C. The frozen material is further dried at −40 to −50° C. by sublimation to remove moisture and to get free flowing powder with moisture content below 5% (w/w).

Example 3

Ragi Probiotic Powders in Guava Juice.

The probiotic powders of the present invention are evaluated for its viability, and pH variability. Fresh Guava fruits are washed and juice is extracted. 100 mg of probiotic powder is inoculated in 100 ml of Guava juice and incubated at 30° C. (room temperature) and 4° C. (refrigeration temperature). Samples are collected at the time intervals of $0^{th}$, $3^{rd}$, $5^{th}$, $7^{th}$, $9^{th}$, $12^{th}$ day for samples stored at 30° C. and weekly for four weeks for samples stored at 4° C. for the assessment of viable count of bacteria and pH. It is evident from the results that the probiotic powder is stable maintaining the viability of the probiotic microorganisms. The results are shown in FIGS. 7A, 7B, 8A & 8B

Example 4

Ragi Probiotic Powders in Apple Juice

The probiotic powders obtained by said process are evaluated for its viability, pH variability. Fresh Apple fruits are washed and juice is extracted. 100 mg of probiotic powder is inoculated in 100 ml of Apple juice and incubated at 30° C. (room temperature) and 4° C. (refrigeration temperature). Samples are collected at the time intervals of $0^{th}$, $3^{rd}$, $5^{th}$, $7^{th}$, $9^{th}$, $12^{th}$ day for samples stored at 30° C. and weekly for four weeks for samples stored at 4° C. for the assessment of viable count of bacteria and pH. It is evident from the results that the probiotic powder is stable maintaining the viability of the probiotic microorganisms. The results are shown in the FIGS. 9A, 9B, 10A & 10B.

Example 5

Ragi Probiotic Powders in Mango Juice

The probiotic powders obtained by said process are evaluated for its viability and pH variability. Fresh Mango fruits are washed and juice is extracted. 100 mg of probiotic powder is inoculated in 100 ml of Mango juice and incubated at 30° C. (room temperature) and 4° C. (refrigeration temperature). Samples are collected at the time intervals of $0^{th}$, $3^{rd}$, $5^{th}$, $7^{th}$, $9^{th}$, $12^{th}$ day for samples stored at 30° C. and weekly for four weeks for samples stored at 4° C. for the assessment of viable count of bacteria and pH. It is evident from the results that the probiotic powder is stable maintaining the viability of the probiotic microorganisms. The results are shown in FIGS. 11A, 11B, 12A & 12B.

The invention claimed is:

1. A dried powder composition comprising solid particles containing:
   i) probiotic microorganisms;
   ii) a carrier phase wherein said probiotic microorganisms are encapsulated within the carrier phase, said carrier phase comprising finger millet extract powder; wherein said dried powder composition contains probiotic microorganisms not less than 1×10$^8$ cfu/gm and wherein the finger millet extract powder also acts as a growth medium for the probiotic microorganisms.

2. The dried powder composition according to claim 1, wherein the probiotic microorganisms are selected from the group consisting of bacteria, yeast and combinations thereof.

3. The dried powder composition according to claim 2, wherein the probiotic microorganisms are bacteria selected from the group consisting of *Lactobacillus acidophilus, Lactobacillus brevis, Lactobacillus rhamnosus* GG, *Lactobacillus bulgaricus, Lactobacillus plantarum, Lactobacillus reuteri, Lactobacillus casei, Lactobacillus paracasei, Bifidobacterium infantis, Bifidobacterium lactis, Bifidobacterium bifidum, Streptococcus thermophiles, Bacillus coagulans* and combinations thereof.

4. The dried powder composition according to claim 2, wherein the probiotic microorganisms are yeast selected from the group consisting of *Saccharomyces cerevisiae, Saccharomyces boulardii*, and combinations thereof.

5. A method of preparing the dried powder composition of claim 1, comprising the steps of:
   i) extracting flaked cereal powder with water to prepare a filtrate;
   ii) wherein extracting flaked cereal powder with water is repeated 4-7 times for 30 minutes each time at ambient temperature;
   iii) inoculating the filtrate obtained in step (ii) with the probiotic microorganisms to provide a mixture;
   iv) incubating the mixture obtained in step (iii) at 37±50 C to provide desired growth of the probiotic microorganisms; and
   v) subjecting the mixture obtained in step (iv) to spray drying or freeze drying to provide the dried powder composition,
   wherein the flaked cereal powder comprises finger millet extract powder.

6. The method according to claim 5, wherein a ratio of flaked cereal powder to water is about 1:3.

7. The method according to claim 5, wherein the filtrate comprises 65-75% carbohydrates, 5-8% protein, 1-2% fat, 15-20% dietary fiber and 2.5-3.5% minerals.

8. The method according to claim 5, wherein the probiotic microorganisms are selected from the group consisting of bacteria, yeast and combinations thereof.

9. The method according to claim 8, wherein the probiotic microorganisms comprise at least one bacteria and one yeast strain.

10. The method according to claim 8, wherein the probiotic microorganisms comprise at least two bacteria and one yeast strain.

11. The method according to claim 8, wherein the probiotic microorganisms are bacteria selected from the group consisting of *Lactobacillus acidophilus, Lactobacillus brevis, Lactobacillus rhamnosus* GG, *Lactobacillus bulgaricus, Lactobacillus plantarum, Lactobacillus reuteri, Lactobacillus casei, Lactobacillus paracasei, Bifidobacterium infantis, Bifidobacterium lactis, Bifidobacterium bifidum, Streptococcus thermophiles, Bacillus coagulans* and combinations thereof.

12. The method according to claim 8, wherein the probiotic microorganisms are yeast selected from the group consisting of *Saccharomyces cerevisiae, Saccharomyces boulardii* and combinations thereof.

13. The method according to claim 5, wherein spray drying is performed at an inlet temperature of about 110±100 C and an outlet temperature of about 85±100 C.

14. The method according to claim 5, wherein the dried powder composition is stable at pH 2, 5, 7 and 8.

15. A composition comprising the dried powder composition of claim 1 as an active ingredient, wherein said composition is in the form of juices, yoghurts, tablets, caplets, capsules, functional food supplements, or dietary supplements.

* * * * *